(12) United States Patent
Minami et al.

(10) Patent No.: US 9,101,657 B2
(45) Date of Patent: Aug. 11, 2015

(54) COMPOSITION COMPRISING TURMERIC EXTRACT AND ZEDOARY EXTRACT

(75) Inventors: Toshiya Minami, Osaka (JP); Masayoshi Kushi, Osaka (JP)

(73) Assignee: HOUSE FOODS CORPORATION, Higashiosaka-Shi (JP)

( * ) Notice: Subject to any disclaimer, the term of this patent is extended or adjusted under 35 U.S.C. 154(b) by 569 days.

(21) Appl. No.: 13/497,992

(22) PCT Filed: Sep. 21, 2010

(86) PCT No.: PCT/JP2010/066279
§ 371 (c)(1), (2), (4) Date: Mar. 23, 2012

(87) PCT Pub. No.: WO2011/037099
PCT Pub. Date: Mar. 31, 2011

(65) Prior Publication Data
US 2012/0177758 A1    Jul. 12, 2012

(30) Foreign Application Priority Data

Sep. 24, 2009    (JP) ................. 2009-218953

(51) Int. Cl.
| | | |
|---|---|---|
| *A61K 36/9066* | (2006.01) | |
| *A23L 1/30* | (2006.01) | |
| *A23L 2/52* | (2006.01) | |
| *A61K 31/12* | (2006.01) | |

(52) U.S. Cl.
CPC ........... *A61K 36/9066* (2013.01); *A23L 1/3002* (2013.01); *A23L 2/52* (2013.01); *A61K 31/12* (2013.01); *A23V 2002/00* (2013.01)

(58) Field of Classification Search
CPC .................... A61K 36/9066; A23V 2200/334
See application file for complete search history.

(56) References Cited

U.S. PATENT DOCUMENTS

| | | | |
|---|---|---|---|
| 6,355,279 | B1 | 3/2002 | Ji et al. |
| 6,497,908 | B1 | 12/2002 | Oshiro |
| 2005/0244522 | A1* | 11/2005 | Carrara et al. |

FOREIGN PATENT DOCUMENTS

| | | |
|---|---|---|
| CN | 1284277 A | 2/2001 |
| CN | 1615144 A | 5/2005 |
| CN | 1736369 A | 2/2006 |
| JP | 4-84870 A | 3/1992 |
| JP | 2000-83618 A | 3/2000 |
| JP | 2000-295985 A | 10/2000 |
| JP | 2001-86931 A | 4/2001 |
| JP | 2001-163793 A | 6/2001 |
| JP | 2003-026588 A | 1/2003 |
| JP | 2005-179213 A | 7/2005 |
| JP | 2006-238730 A | 9/2006 |
| JP | 2007-230882 A | 9/2007 |
| JP | 2009-28042 A | 2/2009 |
| JP | 2009-183206 A | 8/2009 |
| KP | 1020010049804 A | 6/2001 |
| KP | 2002-0089081 A | 11/2002 |
| KP | 1020060090823 A | 8/2006 |
| WO | WO 03/051380 A2 | 6/2003 |
| WO | WO 2005/027949 A1 | 3/2005 |
| WO | 2005/032569 A1 | 4/2005 |
| WO | 2008/055348 A1 | 5/2008 |

OTHER PUBLICATIONS (Kaitei Ban) Kenko Shokuhin Hyakka, 1st edition, 1st print, Bren Shuppan Kabushiki Kaisha, p. 66, Mar. 25, 2003.
Hamano et al., "The effect of beverage containing *Curcuma longa* L. extract on the alcohol metabolism of healthy volunteers", Pharmacometrics, vol. 72, No. 1/2, pp. 31-38, 2007.
International Search Report, dated Nov. 2, 2010, issued in corresponding International Application No. PCT/JP2010/066279.
Office Action issued Jun. 17, 2013, in Korean Patent Application No. 10-2012-7004127.
Chen, Y.P., et al, "A study on the cholagogic effects of commercial turmeric and zedoary articles," Journal of Traditional Medicines, 1997, vol. 14, pp. 96-101.
Ryukyu Syugo Densetsu fused turmeric, http://www.okihoken.com/4hokenshoku.html, Jul. 2008, pp. 2-7E.
Yoshikawa, M., "Physiology of medicated diet 13," Turmeric and Zedoary, Food and Sciences, 2001, vol. 43, No. 5, pp. 49-53.
Chen et al., "Review on Curcuminoids Separated from the *Curcuma* Genus," Journal of Guangxi Teachers Education University (Natural Science Edition) (Jun. 2007), vol. 24, No. 2, pp. 95-101, with English.
Office Action issued Mar. 28, 2013, in Chinese Patent Application No. 201080042749.2.
Korean Office Action, dated Jun. 16, 2014, for Korean Application No. 10-2012-7004127.

(Continued)

*Primary Examiner* — Michele Flood
(74) *Attorney, Agent, or Firm* — Birch, Stewart, Kolasch & Birch, LLP

(57) ABSTRACT

This invention is intended to further improve the effects of alleviating hangover symptoms with the use of a composition comprising a turmeric extract. In particular, this invention is intended to provide a composition that alleviates specific hangover symptoms, such as heartburn and dull headache. The present inventors found that a composition comprising a turmeric (*Curcuma longa*) extract and a zedoary (*Curcuma zedoaria*) extract is capable of effectively suppressing heartburn and dull headache among hangover symptoms. The effects attained with the use of the composition of the present invention are remarkable for a person with low aldehyde dehydrogenase activity.

6 Claims, 1 Drawing Sheet

(56) References Cited

OTHER PUBLICATIONS

Lobo et al., "*Curcuma zedoaria* Rosc. (white turmeric): a review of its chemical, pharmacological and ethnomedicinal properties", Journal of Pharmacy and Pharmacology, vol. 61, 2009, pp. 13-21.

Taiwan Office Action for Appl. No. 099132490 dated Feb. 19, 2014.

China Office Action for Appl. No. 201310349491.6 dated Oct. 28, 2014.

* cited by examiner

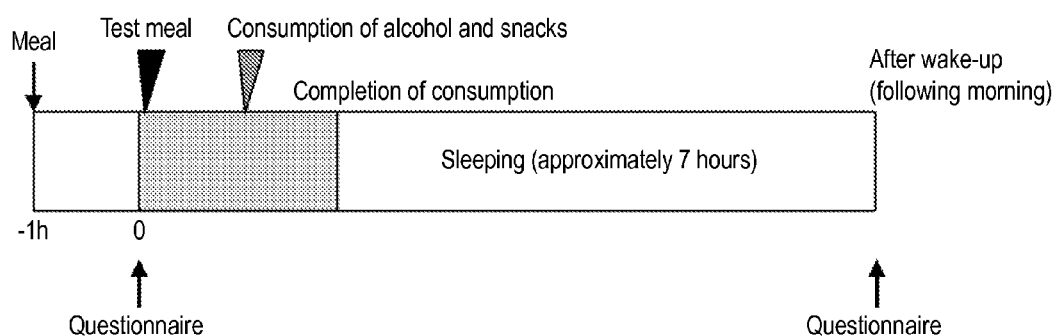

COMPOSITION COMPRISING TURMERIC EXTRACT AND ZEDOARY EXTRACT

TECHNICAL FIELD

The present invention relates to a composition that has effects of alleviating hangover symptoms (heartburn and dull headache, in particular) and that is ingestible in the form of a food, beverage, or pharmaceutical product.

BACKGROUND ART

Turmeric is a medicinal plant of the genus *Curcuma* belonging to the family Zingiberaceae, which is cultivated in tropical and subtropical regions around the world and mainly in Southeast Asia. Many closely related species of turmeric plants are known. Examples of turmeric plants that are known as ingredients of health food in Japan include autumn turmeric (*Aki ukon*), spring turmeric (*Haru ukon*), *Curcuma Domestica* Val. (*Kusuri ukon*), and purple turmeric (*Murasaki ukon*) (Non-Patent Document 1). The academic name for autumn turmeric is *Curcuma longa*. The academic name for purple turmeric is *Curcuma zedoaria*, and it is referred to as "zedoary." In the present invention, autumn turmeric is referred to as "turmeric," and purple turmeric is referred to as "zedoary."

A turmeric rhizome comprises 3% to 5% curcumin (a yellow pigment). A variety of useful properties of turmeric extracts and curcumin are known. For example, Non-Patent Document 2 suggests that a turmeric extract-containing beverage allows an adequate level of "drunkness" originating from alcohol and simultaneously prevents a bad hangover when it is ingested together with an alcohol beverage.

However, it was not known in the past that a liquid composition comprising a turmeric extract has effects of alleviating specific symptoms such as heartburn or dull headache among so-called hangover symptoms that a person experiences when he/she wakes up after alcoholic beverage consumption, and Non-Patent Document 2 does not suggest such effects. In addition, it is not known that such specific symptoms can be alleviated with the use of other compositions.

Patent Document 1 describes a health food product in a dry powder form comprising a dense mixture of crude drug powder (i.e., turmeric powder or zedoary powder) and an agent comprising protease. The technique of Patent Document 1 enables significant improvement in difficulties of handling and ingesting crude drug powders. Patent Document 1 does not suggest the effects of a combination of turmeric powder and zedoary powder. Patent Document 1 does not refer to turmeric or zedoary extracts.

Patent Document 2 describes a method of reducing the odor and bitterness of turmeric rhizomes that is carried out as pretreatment for preparing sliced or powdered turmeric rhizomes. According to Patent Document 2, sliced turmeric rhizomes are soaked in an aqueous solution of γ-aminobutyric acid or the like, and the sliced turmeric rhizomes are then grounded to process turmeric rhizomes. It describes that three types of turmeric species; i.e., spring turmeric, autumun turmeric, and zedoary, can be used for turmeric rhizomes. Patent Document 2 does not suggest the effects of a combination of turmeric powder and zedoary powder. Patent Document 2 does not refer to turmeric or zedoary extracts.

Patent Document 3 describes a vegetable oil containing an oil-soluble turmeric component eluted from turmeric rhizomes. It describes that one or more turmeric species selected from among autumun turmeric, zedoary, and the like can be used. According to the examples of Patent Document 3, grounded autumun turmeric or zedoary is soaked in olive oil to elute an oil-soluble component, as the result of which a turmeric-containing vegetable oil of interest is produced. A small quantity of the turmeric-containing vegetable oil of Patent Document 3 is used for cooking, as with the case of a usual edible oil. It is not considered that a large quantity of turmeric-containing vegetable oil of Patent Document 3 is ingested at one time.

Patent Document 4 describes a composition comprising glutathione and turmeric. Patent Document 4 describes that use of glutathione in combination with turmeric enables provision of a composition that can be applied to a food, pharmaceutical, pet food, or feed product having functions of inhibiting liver damage.

PRIOR ART DOCUMENTS

Patent Documents

[Patent Document 1] JP Patent Publication (kokai) No. 2000-83618 A
[Patent Document 2] JP Patent Publication (kokai) No. 2001-163793 A
[Patent Document 3] JP Patent Publication (kokai) No. 2001-86931 A
[Patent Document 4] JP Patent Publication (kokai) No. 2005-179213 A

Non-Patent Documents

[Non-Patent Document 1] Masayuki Yoshikawa, "*Ukon to Gajutsu*," *Shokuhin to Kagaku* (Turmeric and Zeodry, Food and Sciences), Vol. 43, No. 5, 49-53, 2001
[Non-Patent Document 2] Takuya Hamano et al., "*Ukon chushutsubutsu ga kenjo seijin no alcohol taisha ni oyobosu eikyo no kento*," *Ouyou Yakuri* (Examination of the influence of turmeric extract on alcohol metabolism of healthy individuals, Applied Pharmacology), 72 (1/2), 31-38, 2007

DISCLOSURE OF THE INVENTION

Object to be Attained by the Invention

The present invention is intended to further improve the effects of a composition comprising a turmeric extract for alleviating so-called hangover symptoms that a person experiences when he/she wakes up after alcohol beverage consumption.

The present invention provides a composition that alleviates specific hangover symptoms, such as heartburn or dull headache.

Means for Attaining the Object

The present inventors found that a composition comprising both a turmeric extract and a zedoary extract has significantly higher effects of alleviating hangover symptoms than a composition comprising only a turmeric extract. More specifically, the present inventors found that ingestion of a composition comprising both a turmeric extract and a zedoary extract yields the effects of alleviating heartburn and dull headache among hangover symptoms of a person having low aldehyde dehydrogenase 2 (ALDH2) activity.

The present invention includes the following.
(1) A composition comprising a turmeric (*Curcuma longa*) extract and a zedoary (*Curcuma zedoaria*) extract.

(2) The composition according to (1), which is an orally ingested composition comprising a turmeric (*Curcuma longa*) extract so as to comprise 30 mg or more of curcumin in a single oral dose.

(3) The composition according to (1) or (2), wherein the turmeric (*Curcuma longa*) extract is obtained with the use of an organic solvent.

(4) The composition according to any of (1) to (3), wherein the zedoary (*Curcuma zedoaria*) extract is obtained with the use of a mixed solvent of a hydrophilic organic solvent and water.

(5) The composition according to any of (1) to (4), which is a food, beverage, or pharmaceutical product.

(6) The composition according to (5), which is a liquid composition.

(7) An agent for alleviating a hangover symptom comprising, as active ingredients, a turmeric (*Curcuma longa*) extract and a zedoary (*Curcuma zedoaria*) extract.

(8) The agent for alleviating a hangover symptom according to (7), wherein the hangover symptom is heartburn or dull headache.

(9) The agent for alleviating a hangover symptom according to (7) or (8), which is an orally ingested composition comprising a turmeric (*Curcuma longa*) extract so as to comprise 30 mg or more of curcumin in a single oral dose.

(10) The agent for alleviating a hangover symptom according to any of (7) to (9), wherein the turmeric (*Curcuma longa*) extract is obtained with the use of an organic solvent.

(11) The agent for alleviating a hangover symptom according to any of (7) to (10), wherein the zedoary (*Curcuma zedoaria*) extract is obtained with the use of a mixed solvent of a hydrophilic organic solvent and water.

(12) A method for alleviating a hangover symptom, wherein a person who needs or desires alleviation of a hangover symptom orally ingests the composition according to any of (1) to (5) in an amount effective for alleviating a hangover symptom.

(13) The method according to (12), wherein the composition is orally ingested before alcohol beverage consumption.

(14) The composition according to any of (1) to (5), which is used for alleviating a hangover symptom.

(15) Use of the composition according to any of (1) to (5) for production of a food, beverage, or pharmaceutical product used for alleviating a hangover symptom.

(16) Use of a combination of a turmeric (*Curcuma longa*) extract and a zedoary (*Curcuma zedoaria*) extract for production of a food, beverage, or pharmaceutical composition used for alleviating a hangover symptom.

This description includes part or all of the contents as disclosed in the description and/or drawings of Japanese Patent Application No. 2009-218953, which is a priority document of the present application.

Effects of the Invention

Oral ingestion of the composition according to the present invention enables effective inhibition of so-called hangover symptoms, particularly heartburn and dull headache, that a person experiences when he/she wakes up after alcohol beverage consumption. Such effects of the composition according to the present invention are significant for a person with low aldehyde dehydrogenase 2 (ALDH2) activity.

BRIEF DESCRIPTION OF THE DRAWING

FIG. 1 shows the procedure of a test for confirming the effects of alleviating hangover symptoms.

EMBODIMENTS FOR CARRYING OUT THE INVENTION

1. Turmeric Extract

In the present invention, the term "turmeric extract" refers to a rhizome extract from *Curcuma longa* (academic name), which is commonly known as autumn turmeric.

A turmeric extract can be obtained by extracting a turmeric rhizome with the use of an extraction solvent such as an organic solvent or water and vaporizing the extraction solvent by heating and/or reducing the pressure.

Use of an organic solvent, such as alcohol, hexane, or acetone, is preferable to extract curcumin. It is particularly preferable that curcumin be extracted with acetone. Also, a turmeric extract obtained with the use of a mixed solvent of a hydrophilic organic solvent such as alcohol with water is preferably used. The ratio at which a hydrophilic organic solvent is mixed with water is not particularly limited. For example, such ratio is preferably 10:90 to 90:10, and more preferably 20:80 to 50:50, by weight. Ethanol is preferable as alcohol. A turmeric extract obtained with the use of acetone can be used in combination with a turmeric extract obtained with the use of a mixed solvent of a hydrophilic organic solvent with water.

The composition or agent for alleviating a hangover symptom of the present invention preferably comprises a turmeric extract so as to comprise 30 mg or more, and more preferably 30 mg to 90 mg, of curcumin in a single oral dose. The amount of turmeric extract is, for example, 35 mg or more, and preferably 35 mg to 1,000 mg.

The term "single oral dose" refers to the amount of the composition or agent for alleviating a hangover symptom of the present invention orally ingested in a single administration. Alternatively, the term refers to the total amount of the composition or agent orally ingested at short time intervals (e.g., 10 minutes or shorter, and preferably 5 minutes or shorter) continuously in a plurality of instances of administration. When the composition or agent for alleviating a hangover symptom of the present invention is in the form of liquid composition, for example, the amount thereof is 50 to 500 ml (typically 50 ml, 100 ml, 150 ml, 200 ml, 250 ml, 300 ml, 350 ml, 400 ml, 450 ml, or 500 ml). When the composition or agent is in another form such as a semi-solid (e.g., a gel) or solid form, for example, the amount thereof is 50 to 500 g (typically 50 g, 100 g, 150 g, 200 g, 250 g, 300 g, 350 g, 400 g, 450 g, or 500 g). The term "single oral dose" is used in this sense hereinbelow.

The amount of curcumin in the composition can be determined by dissolving the composition in 50% acetonitrile, subjecting the resultant to centrifugation, and measuring the amount of curcumin in the resulting supernatant via high-performance liquid chromatography (Agilent 1100, Agilent Technologies).

2. Zedoary Extract

In the present invention, the term "zedoary extract" refers to a rhizome extract from *Curcuma zedoaria* (academic name), which is commonly known as purple turmeric.

A zedoary extract can be obtained by extracting a zedoary rhizome with the use of an extraction solvent such as an organic solvent or water and vaporizing the extraction solvent by heating and/or reducing the pressure.

Since zedoary and zedoary powders have a distinctive medicine-like flavor, ingestion thereof is disadvantageously difficult. According to the present invention, however, a composition that does not exhibit a zedoary's distinctive medicine-like flavor and is easy to ingest can be obtained with the use of a zedoary extract.

Use of an organic solvent, such as alcohol, hexane, or acetone, is preferable. It is particularly preferable that extraction be carried out with the use of a mixed solvent of a hydrophilic organic solvent such as alcohol with water. The ratio at which a hydrophilic organic solvent is mixed with water is not particularly limited. For example, such ratio is preferably 10:90 to 90:10, and more preferably 20:80 to 50:50, by weight. Ethanol is preferable as alcohol. A zedoary extract obtained with the use of an organic solvent, such as acetone, can also be used.

The composition or agent for alleviating a hangover symptom of the present invention preferably comprises 50 mg or more, and more preferably 100 mg to 1,000 mg, of a zedoary extract in a single oral dose.

3. Other Components

The composition of the present invention comprises at least the turmeric extract and the zedoary extract described above. It may further comprise other components. Other components are not particularly limited, provided that such components are acceptable in the final forms thereof, such as food, beverage, or pharmaceutical products, and are orally ingestible.

In particular, a liquid composition can be prepared by adding high-fructose corn syrup, cyclic oligosaccharides, acidulants, thickeners, inositol, aroma chemicals, niacin, antioxidants, vitamins, sweeteners, or the like to water, in addition to the turmeric extract and the zedoary extract described above. Cyclic oligosaccharides, acidulants, polysaccharide thickeners, and sweeteners have effects of masking the bitterness of the turmeric extract and the zedoary extract.

Examples of acidulants include citric acid, malic acid, gluconic acid, tartaric acid, and a salt of any thereof.

Examples of thickeners include polysaccharide thickeners, such as gellan gum, xanthan gum, pectin, and guar gum.

Examples of sweeteners include saccharides, such as fructose, glucose, and liquid sugar, and high intensity sweeteners, such as honey, sucralose, acesulfame potassium, thaumatin, and aspartame.

Examples of antioxidants include vitamin C and enzyme-treated rutin.

Examples of vitamins include vitamin $B_1$, vitamin $B_6$, and vitamin E.

4. Composition and Application Thereof.

The composition of the present invention can be used in the form of a food, beverage, or pharmaceutical composition having effects of alleviating so-called hangover symptoms that a person experiences when he/she wakes up after alcoholic beverage consumption.

The form of the composition of the present invention is not particularly limited. It is preferably in the form of a liquid, solid, or semisolid composition that is suitable for oral ingestion. A liquid composition is particularly preferable. A liquid composition may be provided in the form of a liquid food (beverage), and it may be provided in the form of a liquid pharmaceutical product for oral administration, with a beverage being preferable. A liquid composition is mainly composed of water, and it comprises 90% by weight or more water, for example. Such liquid composition can be contained in a bottle, an aluminum or steel container, a PET bottle, or another container and prepared in the form of a product. Alternatively, the composition of the present invention may be granulated or tableted, and the resultant may be introduced into an adequate container to prepare a product.

The present invention also relates to a method for alleviating a hangover symptom, wherein a person who needs or desires alleviation of a hangover symptom orally ingests the composition of the present invention in an amount effective for alleviating a hangover symptom.

The present invention also relates to the composition of the present invention used for alleviating a hangover symptom.

The present invention also relates to the use of the composition of the present invention for production of a food, beverage, or pharmaceutical composition used for alleviating a hangover symptom.

The present invention also relates to the use of a combination of a turmeric extract and a zedoary extract for production of a food, beverage, or pharmaceutical composition used for alleviating a hangover symptom.

According to these embodiments of the present invention, a target person orally ingests the composition of the present invention or the combination of a turmeric extract and a zedoary extract in an amount effective for alleviating a hangover symptom. The "amount effective for alleviating a hangover symptom" is typically the amount of said composition or said combination comprising a turmeric extract so as to comprise 30 mg or more, and preferably 30 mg to 90 mg, of curcumin (e.g., 35 mg or more, and preferably 35 mg to 1,000 mg, of the turmeric extract) and comprising 50 mg or more, and preferably 100 mg to 1,000 mg of the zedoary extract. Oral ingestion is preferably carried out before a hangover symptom develops, and more preferably before a person consumes an alcoholic beverage (e.g., 2 hours to immediately before alcohol consumption).

EXAMPLES

In this test, the effects of the composition of the present invention comprising a turmeric extract and a zedoary extract for preventing a hangover was examined.

1. Test Beverages

Beverages 1 to 3 were employed for the test.

The test subjects ingested the cooled test beverages once in an amount of 100 ml/dose.

TABLE 1

Components incorporated into beverage compositions used for test (unit: g)

| | Beverage 1: Beverage of the invention | Beverage 2: Glutathione-containing beverage | Beverage 3: Control beverage |
|---|---|---|---|
| Functional components | Turmeric + zedoary | Turmeric + glutathione | Turmeric |
| Ethanol-water extract of turmeric | 0.15 | 0.15 | 0.15 |
| Organic solvent extract of turmeric | 0.13 | 0.13 | 0.1 |
| Vitamin C | 0.01 | 0.01 | 0.01 |
| Vitamin E | 0.01 | 0.01 | 0.01 |
| Niacin | 0.01 | 0.01 | 0.01 |
| Vitamin B6 | 0.001 | 0.001 | 0.001 |
| High-fructose corn syrup | 5 | 5 | 5 |
| Citric acid | 0.3 | 0.3 | 0.3 |
| Xanthan gum | 0.1 | 0.1 | 0.1 |
| Sucralose | 0.006 | 0.006 | 0.006 |
| Aroma chemical | 0.1 | 0.1 | 0.1 |
| Ethanol-water extract of zedoary | 0.13 | — | — |
| Glutathione-containing yeast extract | — | 0.81 | — |
| Water | 94.053 | 93.373 | 94.213 |
| Total | 100 | 100 | 100 |

The ethanol-water extract of turmeric was obtained by extracting a rhizome part of turmeric (*Curcuma longa*) with the use of hydrous ethanol (i.e., an aqueous solution that contains 30% by weight ethanol) and reducing the pressure to vaporize ethanol.

The organic solvent extract of turmeric was obtained by extracting a rhizome part of turmeric (*Curcuma longa*) with the use of acetone and reducing the pressure to vaporize acetone. The organic solvent extract of turmeric contains 30% by weight curcumin.

The ethanol-water extract of zedoary was obtained by extracting a rhizome part of zedoary (*Curcuma zedoaria*) with the use of hydrous ethanol (i.e., an aqueous solution that contains 30% by weight ethanol) and reducing the pressure to vaporize ethanol.

The glutathione-containing yeast extract obtained from Torula yeast with high glutathione content was used. This glutathione-containing yeast extract contains 10% by weight or more glutathione.

2. Test Subject

Test subjects were selected from among men who were capable of consuming an alcoholic beverage. Those incapable of consuming an alcoholic beverage (self-reported), those regularly visiting the hospital, those on medication, those afflicted with renal or hepatic diseases, and those with various types of hypersensitivity were excluded.

The test subjects were divided into those homozygous for the aldehyde dehydrogenase 2 (ALDH2) genes and those heterozygous therefor via alcohol patch testing. Eight (8) heterozygous subjects were subjected to the test described below.

3. Test Method

The effects of test beverages for alleviating a hangover were examined with the following procedure.

The subjects ingested the test beverages at least 1 hour after a meal.

The subjects each consumed the entire amount of an alcoholic beverage immediately after they had ingested the test beverage (the duration of alcohol consumption was not limited, and it should be 50 minutes or longer and approximately 3 hours). When the subjects were unable to drink the entire amount thereof; the undrunk portions were recovered, and the amount consumed was measured.

Subjects consumed whisky as the alcohol. At the same time, they were allowed to drink water in an amount up to approximately twice the amount of whisky and to eat snacks (subjects were allowed to eat any snacks, but they had to eat the same type of snack every time (e.g., potato chips)).

The amount of alcohol ingested was determined based on the acceptable intake of each subject (self-reported), although the upper limit was set at 1.5 g of alcohol per 1 kg of body weight.

The subjects went to sleep after alcohol consumption and slept for approximately 7 hours.

Questionnaires on hangover symptoms were given before the subjects ingested the test beverages and immediately after they woke up.

The times at which the subjects answered the questionnaires, contents of snacks, and the number of times the subjects used the restroom were recorded.

The following behavior was prohibited:

Eating and drinking after a meal (the designated amount of water and snacks could be ingested during alcohol consumption)

Alcohol consumption on the day before the test

Other clinical tests on the day before or the day following the test

Driving on the following morning

FIG. 1 schematically shows the procedure of the above test.

4. Test Schedule

The tests described above were conducted. At the outset, the test subjects ingested the test beverage 3, and the subjects were then tested for the beverages 1 and 2 when hangover symptoms were observed. The tests were conducted at intervals of at least 3 days, so that the subjects would recover from hangover symptoms.

When hangover symptoms were not observed in the first test in which the test beverage 3 was ingested, the conditions of alcohol consumption were reconsidered.

5. Questionnaire Evaluation Items

The subjects were asked to fill in the questionnaires with the results of self-evaluation by the VAS method regarding 5 symptoms: i.e., sickness, nausea, heartburn, headache, and dull headache.

The visual analog scale (VAS) method is a type of evaluation involving digitalization of the degrees of subjective symptoms. With this method, a subject linearly indicates his or her condition on a line the right end of which is designated as the best condition and the left end of which is designated as the worst condition. This method is extensively employed in clinical medicine for subjective evaluation, and it is employed for comparisons of the conditions of a single subject before and after administration, in particular.

6. Test Results

Regarding each evaluation item for the tests in which the subjects ingested the beverages, the difference between VAS values immediately after wake-up and immediately before ingestion (i.e., before the test) of each subject was determined ([VAS value immediately after wake-up]–[VAS value immediately before ingestion]; hereafter referred to as "difference in VAS value").

The difference in VAS value for each evaluation item determined in the test in which the beverage 1 was ingested was likely to be less than that corresponding to that for the test in which the beverage 3 was ingested. The difference in VAS value for each evaluation item determined in the tests in which the beverages 1 and 2 were ingested was compared with that for the same evaluation item attained in the test in which the beverage 3 was ingested. The results of examination of significant differences (i.e., p values) are shown in Table 2 below.

TABLE 2

| | Sickness | Nausea | Heartburn | Headache | Dull headache |
|---|---|---|---|---|---|
| Beverage 1 | 0.344 | 0.383 | 0.008* | 0.413 | 0.028* |
| Beverage 2 | 0.130 | 0.732 | 0.534 | 0.373 | 0.203 |

*Effects were observed with a significant difference of 5% ($p < 0.05$).

The beverage 1 containing a turmeric extract and a zedoary extract was found to selectively alleviate "heartburn" and "dull headache" as hangover symptoms in a more effective manner than the beverage 2 and the beverage 3 comprising, as an functional component, a turmeric extract alone.

All publications, patents, and patent applications cited herein are incorporated herein by reference in their entirety.

The invention claimed is:

1. A method for alleviating a hangover symptom, comprising administering orally to a person who needs or desires alleviation of a hangover symptom a composition comprising a turmeric (*Curcuma longa*) extract and a zedoary (*Curcuma zedoaria*) extract in an amount effective to alleviate a hangover symptom, wherein the zedoary (*Curcuma zedoaria*) extract is a hydrophilic organic solvent and water zedoary (*Curcuma zedoaria*) extract.

2. The method according to claim 1, wherein the composition comprises 30 mg or more of curcumin from the turmeric (*Curcuma longa*) extract.

3. The method according to claim 1, wherein the turmeric (*Curcuma longa*) extract is an organic solvent turmeric (*Curcuma longa*) extract.

4. The method according to claim 1, wherein the composition is in the form of a food, beverage, or pharmaceutical product.

5. The method according to claim 1, wherein the hangover symptom is heartburn or a dull headache.

6. The method according to claim 1, wherein the composition is administered orally before alcohol beverage consumption.

* * * * *